US011116810B2

(12) United States Patent
Botto et al.

(10) Patent No.: US 11,116,810 B2
(45) Date of Patent: Sep. 14, 2021

(54) METHODS FOR TREATMENT OF SKIN AND SKIN APPENDAGES WITH A LINSEED EXTRACT AS AN ACTIVE AGENT ACTIVATING THE SYNTHESIS OF ANTIMICROBIAL PEPTIDES

(71) Applicant: ISP INVESTMENTS INC., Wilmington, DE (US)

(72) Inventors: Jean-Marie Botto, Garbejaire (FR); Nouha Domloge, Valbonne (FR); Frederique Portolan, Valbonne (FR)

(73) Assignee: ISP INVESTMENTS LLC, Wilmington, DE (US)

( * ) Notice: Subject to any disclaimer, the term of this patent is extended or adjusted under 35 U.S.C. 154(b) by 856 days.

(21) Appl. No.: 14/437,996

(22) PCT Filed: Oct. 25, 2013

(86) PCT No.: PCT/FR2013/052555
§ 371 (c)(1),
(2) Date: Apr. 23, 2015

(87) PCT Pub. No.: WO2014/064397
PCT Pub. Date: May 1, 2014

(65) Prior Publication Data
US 2015/0290273 A1 Oct. 15, 2015

(30) Foreign Application Priority Data
Oct. 26, 2012 (FR) ........................................ 1260235

(51) Int. Cl.
*A61K 36/55* (2006.01)
*A61Q 19/00* (2006.01)
*A61K 8/64* (2006.01)
*A61K 8/9789* (2017.01)
*A61K 9/00* (2006.01)
*A61Q 17/00* (2006.01)

(52) U.S. Cl.
CPC .............. *A61K 36/55* (2013.01); *A61K 8/645* (2013.01); *A61K 8/9789* (2017.08); *A61K 9/0014* (2013.01); *A61Q 17/005* (2013.01); *A61Q 19/00* (2013.01); *A61Q 19/005* (2013.01)

(58) Field of Classification Search
CPC ...... A61K 36/55; A61K 8/645; A61K 8/9789; A61K 9/0014; A61K 8/97; A61P 17/00; A61P 31/00; A61P 31/04; A61Q 17/005; A61Q 19/00; A61Q 19/005

USPC .......................................................... 424/768
See application file for complete search history.

(56) References Cited

U.S. PATENT DOCUMENTS

| 8,349,803 B2 | 1/2013 | Dal Farra et al. |
| 10,821,069 B2 * | 11/2020 | Portolan ............. A61K 8/9728 |
| 2009/0005300 A1 | 1/2009 | Hodges et al. |
| 2010/0196293 A1 | 8/2010 | Dal Farra et al. |
| 2010/0215591 A1 | 8/2010 | Stone et al. |
| 2010/0279946 A1 | 11/2010 | Dal Farra et al. |

FOREIGN PATENT DOCUMENTS

| FR | 2918893 | | 1/2009 | |
| FR | 2918893 A1 * | | 1/2009 | ............. A61K 8/645 |
| FR | 2956818 | | 9/2011 | |
| FR | 2956818 A1 * | | 9/2011 | ............. A61K 36/55 |

OTHER PUBLICATIONS

Firas A. Al-Bayati, "Antibacterial Activity of *Linum usitatissimum* L. Seeds and Active Compound Detection"(Raf. Journal of Science, vol. 18, No. 2, pp. 27-36, 2007). (Year: 2007).*
Gambichler et al. "Differential mRNA Expression of Antimicrobial Peptides and Proteins in Atopic Dermatitis as compared to Psoriasis Vulgaris and Healthy Skin", Int. Arch. Allergy Imminol. 2008; 147:17-24) (Year: 2008).*
PCT, International Search Report, International Application No. PCT/FR2013/052555, (dated Feb. 17, 2014; dated Mar. 6, 2014).
Kaithwas, G. et al., "*Linum usitatissimum* (linseed/flaxseed) fixed oil: antimicrobial activity and efficacy in bovine mastitis," Inflammopharmacology, vol. 19, No. 1, pp. 45-52 (2011).
Al-Bayati, F.A., "Antibacterial Activity of *Linum usitatissimum* L. Seeds and Active Compound Detection," Raf. Jour. Sci., vol. 18, No. 2, pp. 27-36 (2007).
Nand, P. et al., "Antimicrobial Investigation of *Linum usitatissimum* for the Treatment of Acne," Natural Product Communications, vol. 6, No. 11, pp. 1701-1704 (2011).

(Continued)

*Primary Examiner* — Aaron J Kosar
(74) *Attorney, Agent, or Firm* — Thompson Hine LLP

(57) ABSTRACT

Methods for the treatment of irritations of the skin and skin appendages caused by microbial stresses are disclosed. The methods include providing a composition comprising a linseed extract, obtained from hydrolysis of linseed proteins, as an active antimicrobial agent in a physiologically acceptable medium, and topically applying the linseed extract onto the skin in need thereof. The methods may be useful in the cosmetic and pharmaceutical field and, more particularly, in the field of dermatology. Cosmetic methods for reinforcing the chemical barrier function of healthy and/or sensitive skin and skin appendages are also disclosed that include the same or similar composition and steps.

5 Claims, 1 Drawing Sheet

(56) References Cited

OTHER PUBLICATIONS

Xu, Y. et al., "Antifungal Activity Stability of Flaxseed Protein Extract Using Response Surface Methodology," Journal of Food Science, Wiley-Blackwell Publishing, Inc., US, vol. 73, No. 1, pp. M9-M14 (2008).
Author Mohammad Najmul Ghani Khan, Title of publication—Khazaain-al-Advia. vol. I, Page(s) being submitted—5 (pp. 4-8), (Ref. pg. No. of publication: 561), Publication Date—1911 AD, Publisher—Nadeem Yunus Printer/Sheikh Mohd Basheer & Sons, Place of Publication—Lahore.
Author Mohammad Najmul Ghani Khan, Title of publication—Khazaain-al-Advia. vol. I, Page(s) being submitted—5 (pp. 9-13), (Ref. pg. No. of publication: 562), Publication Date—1911 AD, Publisher—Nadeem Yunus Printer/Sheikh Mohd Basheer & Sons, Place of Publication—Lahore.
Author Abu Ali Ibn-e-Sina, Title of publication—Al-Qaanoon-fil-Tibb. vol. II, Page(s) being submitted—5 (pp. 14-18), (Ref. pg. No. of publication: 76), Publication Date—1987 AD, Publisher—Institute of History of Medicine and Medical Research, Place of Publication—New Delhi, India.

* cited by examiner

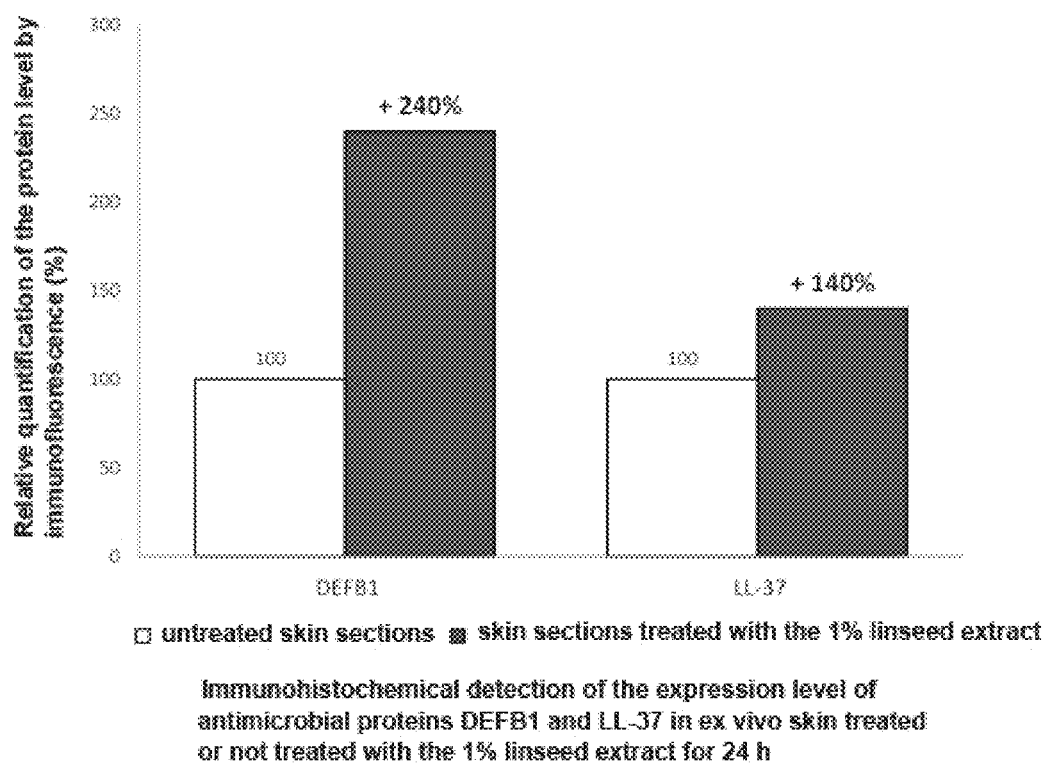
Immunohistochemical detection of the expression level of antimicrobial proteins DEFB1 and LL-37 in ex vivo skin treated or not treated with the 1% linseed extract for 24 h

METHODS FOR TREATMENT OF SKIN AND SKIN APPENDAGES WITH A LINSEED EXTRACT AS AN ACTIVE AGENT ACTIVATING THE SYNTHESIS OF ANTIMICROBIAL PEPTIDES

This invention pertains to the fields of cosmetics and pharmaceuticals, and more specifically the field of dermatology. This invention relates to a linseed extract for use in protecting the skin and skin appendages from microbial stresses.

The invention also relates to a linseed extract for use in increasing the expression level of antimicrobial peptides.

The term "skin appendages" according to the invention encompasses all keratin appendages present at the surface of the body, in particular body hair, eyelashes, eyebrows, nails and hair.

The main function of the epidermis is to provide a protective barrier between the organism and the external environment. At the epidermis, two types of barriers are at play: a physical barrier formed by the skin itself, ensured by strong intercellular cohesion (desmosomes, tight junctions) and the abrasion resistance of the keratin cells, and a chemical barrier formed by skin secretions (sebum, sweat), which makes it possible to fight allergens and irritants and which performs an antibacterial role owing to the acid pH of the stratum corneum and the presence of hydrolytic enzymes and antimicrobial peptides. The cells of the immune system form a third defensive barrier capable of removing microorganisms that manage to pass through the epidermis.

The skin, in direct contact with the external environment, is exposed to numerous microorganisms that colonize the superficial layers of the epidermis and the appendages (hair follicles, sebaceous glands and sweat glands). The skin maintains a stable ecosystem, favorable to certain microorganisms, the growth requirements of which are compatible with the local conditions. The human skin may have more than one thousand species of bacteria and the total number is estimated at $10^{12}$ bacteria. The cutaneous microbial flora of a healthy subject is a commensal microbial flora that includes resident cutaneous flora and transient cutaneous flora.

The resident cutaneous flora is dominated by gram-positive species, in particular bacteria of the *Staphylococcus* genus (for example *S. epidermidis*), *Corynebacterium* (for example *C. minutissimum*) and *Propionibacterium* (for example, *P. acnes*). Other bacteria of the resident flora are, for example, certain micrococci or the *Brevibacterium* genus.

The transient cutaneous flora is more polymorphous and may comprise potentially pathogenic germs, coming from the digestive tract or the nasopharynx or the environment. It includes enterococci, golden staph and gram-negative bacteria (in particular *Acinetobacter, Enterobacter, Pseudomonas*) and fungi (for example, *C. Albicans*).

The bacteria of the transient microbial flora generally reside for a brief period on the skin where the environment is unfavorable to them. However, they may act as opportunistic pathogens and cause infections in individuals with weakened defense systems, for example in the case of systemic diseases (immunodepressed, diabetic patients) or in the case of an alteration of the barrier function of the skin (psoriasis or atopic dermatitis).

Any skin lesion leads to a weakening of its natural line of defense. The skin is then sensitive to attacks from pathogenic microorganisms. In addition, the resident or transient cutaneous microbial flora may then act as opportunistic pathogens, colonize the lesion, then, if the conditions are favorable, cause a local and/or systemic infectious process.

The commensal cutaneous microbial flora helps to maintain the ecosystem and the health of the skin by participating in the chemical barrier function of the skin. In fact, the resident germs of the skin play an important role in the skin's resistance to colonization by pathogenic microorganisms because they compete for space and food with pathogenic bacteria, release antibacterial substances (inhibitors, creation of unfavorable pH conditions or receptor modification), which slow the growth of pathogenic bacteria and continuously stimulate the immune system, enabling the bacterial flora of the skin and skin appendages to be regulated.

In addition, the keratinocytes and sebocytes also participate in the equilibrium of the resident cutaneous flora and protect the skin from pathogenic microorganism by expressing, among other things, Antimicrobial Peptides (AMP). AMPs are a family of polypeptides of fewer than 100 amino acids that have a spectrum of activity against broad pathogenic microorganisms, including bacteria, fungi, enveloped viruses and protozoa. The mechanisms of action of AMPs include a direct antimicrobial activity and the initiation of a host response, which leads to the release of cytokines, inflammation, angiogenesis and re-epithelialization. The mechanism of the direct antimicrobial activity of the AMPs involves their attachment to the membrane of the target microorganisms in the form of multimeric pores, which leads to lysis of target microorganisms.

In humans, two groups of AMPs are predominantly expressed by the skin: defensins (DEFBs) and epithelial cathelicidins, which are cationic mediators of the non-specific innate immune system.

Human cathelicidin hCAP18 is an inactive propeptide. Its C-terminal fragment LL37 has an antimicrobial activity with a broad spectrum of activity and modulates the immune response. In the epidermis, kallikreins, primordial enzymes involved in the desquamation process, are responsible for the maturation of cathelicidin into LL-37 post-transcriptionally.

The defensins are small cationic peptides of fewer than 50 amino acids expressed in the form of precursor prepropeptides. The defensin family may be divided into two groups: α-defensins (which are located in the neutrophiles and the Paneth cells of the small intestine) and β-defensins expressed at the surface of the epithelial cells. Six β-defensins called DEFB1 to 6 have been identified in human tissue, including DEFB1, 2 and 3 expressed in the skin. DEFB1, 2 and 3 are constitutively expressed by the keratinocytes of the upper layers of healthy skin and participate in the chemical barrier of the skin by inhibiting the growth of pathogenic microorganisms and their invasion of the skin surface.

In this context, the properties of AMPs appear to be particularly beneficial for reinforcing the protective function of the skin from microbial stresses and for promoting equilibrium of the resident microflora of the skin.

A certain number of substances introduced in cosmetic or pharmaceutical products for topical application have appeared. Documents US 2009/0005300 and US 2010/0215591 describe natural or synthetic AMPs and the use thereof as antimicrobials in pharmaceutical or cosmetic compositions. However, there is still a need to develop new ingredients making it possible to product the health and integrity of the skin functions. In addition, there is still a need to develop new ingredients for improving the aesthetic appearance of the skin, in particular for people with sensitive and irritable skin.

This invention is intended to propose an active agent having the advantage of being of natural origin and making it possible to protect the commensal microbial flora of the skin. The inventors have demonstrated an antimicrobial activity, of a linseed extract, described in this invention. It has in particular been demonstrated that this linseed extract, when applied to the skin, has a strong protective activity with respect to the commensal bacterial flora of the skin and aggressions by infectious agents that cause skin irritation reactions.

This new active principle, capable of increasing the expression level of AMPs of the skin thus makes it possible to consider new cosmetic and therapeutic perspectives.

According to a first aspect, this invention concerns a linseed extract as an active antimicrobial agent.

The invention and resulting advantages will be better understood in view of the description.

The invention addresses mammals in general, and more specifically human beings.

The term "antimicrobial" or "protection from microbial stresses" relates to the death of microorganisms, the inhibition of their growth or the prevention of their growth "Inhibition of the growth of pathogenic microorganisms" means the reduction in the growth of pathogenic microorganisms, for example in terms of reduction of the number of colonies and/or the size of the pathogenic microorganism colonies, while the phrase "prevention of the growth of microorganisms" refers to the stopping of microorganism growth.

"Microorganisms" or "microbes" refer to any organism found in the phylogenetic domains of achaebacteria or bacteria, as well as unicellular and filamentous fungi (for example yeast), unicellular or filamentous algae, uni- and pluricellular parasites and viruses.

According to specific features, the invention relates to a linseed extract for use in the protection of skin and skin appendages from microbial stresses.

The use of linseed extract, or a composition containing it, on skin having an altered chemical barrier function or weakening of the local immune system, will enable the skin and skin appendages to be protected and make it possible to better resist attacks by pathogenic or opportunistic microorganisms.

According to specific features, the invention relates to a linseed extract for its use in increasing the expression level of antimicrobial peptides.

Preferably, the invention relates to a linseed extract for increasing the cellular expression level of defensins and/or cathelicidin.

According to specific features, the invention relates to a linseed extract for its use in stimulating the immune defenses of the skin.

According to specific features, the invention relates to a linseed extract for its use in the treatment of *Staphylococcus aureus* infections of the skin and skin appendages.

The invention also relates to a linseed extract for its use in the treatment of atopic dermatitis and/or rosacea of the skin.

Rosacea is a skin condition caused by bacteria, possibly associated with factors rendering the skin protection systems vulnerable. Atopic dermatitis is also a skin condition in which the expression of cathelicidin is abnormally diminished.

Advantageously, the linseed extract according to the invention makes it possible to stimulate the production of cathelicidin-type AMPs by the skin cells, without causing a toxic or allergic reaction of the skin.

According to a second aspect, the invention relates to the use of a linseed extract for reinforcing the chemical barrier function of the skin and skin appendages.

"Reinforcing the chemical barrier function" means that the application of a linseed extract or a cosmetic composition containing it on healthy skin and/or sensitive skin makes it possible to increase the cellular expression level of AMPs. Linseed extract has a localized action at the epidermis and makes it possible to calm skin irritation such as redness or discomfort of sensitive skin.

According to specific features, the invention relates to the use of a linseed extract for protecting the commensal microbial flora and/or limiting the imbalance of the commensal microbial flora of the skin and skin appendages.

Advantageously, the cosmetic use of the linseed extract according to the invention makes it possible to maintain a good chemical barrier function of the skin by locally stimulating, at the epidermis, the expression of AMPs, which helps to maintain the equilibrium and favorable conditions of the ecosystem of the commensal microflora of the skin.

The linseed extract used according to the invention may be any type of linseed extract.

According to preferred features, the linseed extract comes from the hydrolysis of linseed proteins.

More preferably, the linseed extract contains at least 0.1 to 5 g/l of peptide compounds by weight of dry extract, 0.1 to 2 g/l of sugar by weight of dry extract and essentially includes peptide compounds of molecular weight below 5 kDa, preferably with a molecular weight below 2.5 kDa.

The term "peptide" refers to a chain of two or more amino acids linked with one another by peptide bonds or by modified peptide bonds; the term "polypeptide" refers to a peptide of larger size; the term "peptide compounds" refers to protein fragments, peptides and free amino acids present in the mixture.

The term "hydrolysate or resulting from hydrolysis" refers to any substance or mixture of substances, or isolated preparation, obtained after hydrolysis of plant material.

To perform the extraction, it is possible to use the whole plant, or a specific part of the plant (leaf, seed, etc.).

More specifically according to the invention, one of the numerous plants of the Linaceae family, of the *Linum* genus (linseed) is used. The *Linum* genus includes more than 200 species growing in the northern hemisphere. They are herbaceous plants with fibrous stems, simple leaves and 5-petal flowers. Preferably according to the invention, the cultivated species *Linum usitatissimum* L is used. The linseed extract (*Linum*) according to the invention is preferably a peptide extract resulting from the hydrolysis of proteins extracted from linseed seeds and preferably the seed removed from its shell by a shelling step.

Any method of extraction or purification known to a person skilled in the art may be used to prepare the linseed extract according to the invention.

Preferably, the linseed extract is obtained by a process that includes:
  a step of extracting proteins of plant origin,
  a step of controlled hydrolysis, which releases biologically active peptide compounds.

Many proteins found in the plants are capable of containing biologically active peptide compounds in their structures. Controlled hydrolysis makes it possible to remove these peptide compounds. It is possible, but unnecessary in order to carry out the invention, either first to extract the proteins concerned and then to hydrolyze them, or first to perform the hydrolysis on a raw extract and then to purify the peptide compounds.

A specific embodiment of the process for obtaining the linseed extract according to the invention is described below.

In a first step, the plant is ground by means of a plant grinder. The powder thus obtained may subsequently be "delipidated" by means of a conventional organic solvent (such as, for example, an alcohol, hexane or acetone).

In a second step, the extraction of the plant proteins is performed by a conventional process. The ground material of the plant is suspended in an alkaline solution containing an adsorbent product of the insoluble polyvinylpolypyrrolidone (PVPP) (0.01-20%) type; in fact, it has been observed that the subsequent hydrolysis and purification operations were facilitated by this means. The concentration of phenol substances, interacting with the proteins, is thus reduced.

The soluble fraction is collected after centrifugation and filtration steps, the raw solution then constituting a first form of the extract containing the proteins, carbohydrates and possibly lipids.

According to a specific embodiment of the process, the proteins may then be precipitated by varying the ionic force by acidifying the medium, which makes it possible to remove the soluble components. The precipitate is then washed by means of an organic solvent such as, for example, ethanol or butanol, then the solvent is evaporated by vacuum drying. The protein-rich precipitate is then placed in solution in water or another solvent and then constitutes a more purified form of the hydrolysate.

The step of extracting proteins from the plant can also be performed in a neutral or acid medium, always in the presence of polyvinylpolypyrrolidone. After a filtration step, a precipitation step may be performed in a specific implementation, by means of a conventional precipitation agent such as salts (sodium chloride, ammonium sulfate) or an organic solvent (alcohol, acetone). The precipitate obtained may be separated from the precipitation agents by dialysis after being placed in solution in water or another solvent.

The soluble fraction, including proteins, carbohydrates and possibly lipids, is collected after centrifugation and filtration steps. This raw solution is then hydrolyzed under controlled conditions in order to generate peptide compounds, polypeptides and soluble peptides. Hydrolysis is defined as being a chemical reaction involving the cleaving of a molecular by water, this reaction being capable of being performed in a neutral, acid or basic medium. According to the invention, the hydrolysis is performed chemically and/or advantageously by proteolytic enzymes.

According to specific features, hydrolysis is performed by a protease or a mixture of proteases and/or a cellulose or a mixture of cellulases.

According to preferred features, a mixture of enzymes containing the following is used:
  endoproteases of plant origin (for example, papain, bromelain, ficin, etc.) and/or from microorganisms (*Aspergillus, Rhizopus, Bacillus*, Alcalase®, etc.),
  and/or a cellulase or a mixture of cellulases (for example Celluclast® CL).

Advantageously, the cellulases enable better hydrolysis of the cellular wall of the linseed, which increases the accessibility of the proteins and facilitates filtration. In fact, the cellulases enable hydrolysis of the cellular walls with small oligosaccharides. The conjoint action of the cellulases and proteases then leads to polypeptides having a low molecular weight below 5 kDa and more specifically a significant fraction below 2.5 kDa. Once these different hydrolyses have been performed, a thermal deactivation step is necessary in order to inactivate the enzymes.

For the same reasons as above, i.e. the removal of polyphenol substances, a quantity of polyvinylpolypyrrolidone is added to the reaction medium in this controlled hydrolysis step.

After filtration, the solution obtained constitutes a first advantageous form of linseed peptide extract according to the invention. The linseed peptide extract can again be purified in order to select the molecular weights and the nature of the peptides generated. The fractionation may be performed advantageously by ultrafiltration and/or by a chromatographic method.

The use of peptide extracts, and in particular peptide extracts of low molecular weight, has numerous advantages in cosmetics. Aside from the generation of peptide compounds that did not exist in the starting protein mixture, the hydrolysis and purification make it possible to obtain a mixture of more stable peptide compounds, with a composition that is more easily reproducible and not causing allergic reactions in cosmetics.

According to specific features, the linseed extract according to the invention essentially includes peptide compounds having a low molecular weight. Preferably, the linseed peptide extract according to the invention essentially includes peptide compounds having a molecular weight below 2.5 kDa.

Any one of the more or less purified forms of the hydrolysate is then solubilized in water or in any mixture containing water, then sterilized by ultrafiltration.

The linseed extract, obtained according to the invention, is qualitatively and quantitatively analyzed for its physicochemical characteristics and its peptide compound content. The term peptide compounds refers to the protein fragments, the peptides and the free amino acids present in the mixture. The peptides, amino acids and protein fragments are dosed according to conventional techniques well known to a person skilled in the art.

Thus, according to an advantageous embodiment of the invention, the linseed extract has a pH of between 4 and 5, and preferably between 4 and 4.5. Advantageously, this acid pH promotes the dissolution of proteins in water and stabilizes the proteins. The linseed extract according to the invention has a dry weight of between 0.1 and 8 g/l, and preferably between 0.1 and 5 g/l, and includes:
  between 0.1 and 5 g/l of peptide compounds by weight of dry extract,
  and between 0.1 and 2 g/l of sugar by weight of dry extract.

The extract is then diluted in water or in any mixture of solvent containing water, then sterilized by sterilizing filtration (0.2 µm).

According to specific features, the extract is diluted in one or more physiologically acceptable solvents, such as water, glycerol, ethanol, propanediol, butylene glycol, dipropylene glycol, ethoxylated or propoxylated diglycols, cyclic polyols or any mixture of these solvents. "Physiologically acceptable" means that the chosen solvent is suitable for coming into contact with the skin without causing toxicity or intolerance reactions.

Preferably, after dilution, the linseed extract includes:
  between 1.5 and 3.5 g/l of peptide compounds by weight of dry extract,
  and around 0.3 g/l of sugar by weight of dry extract.

The sugar content is even more preferably below 0.3 gain the linseed extract according to the invention.

After this dilution step, the extract may be encapsulated or included in a cosmetic or pharmaceutical vector such as liposomes or any other microcapsules used in the field of cosmetics or adsorbed on powder organic polymers, mineral supports such as talcs and bentonites, and more generally solubilized in, or fixed on, any physiologically acceptable vector.

The linseed extract according to the invention may be used in a cosmetic or pharmaceutical composition. The composition may include a quantity of linseed extract necessary for obtaining the desired result, namely: protecting the skin and skin appendages from microbial stresses, protecting the bacterial flora of the skin and skin appendages, stimulating the immune defenses of the skin and stimulating the expression of AMPs.

According to an advantageous embodiment of the invention, the linseed extract according to the invention is present in the composition at a concentration of between 0.0001% to around 20%, and preferably at a concentration of between 0.05% and around 5%, and even more preferably at a concentration of between 1% and around 3% with respect to the total weight of the final composition.

The compositions according to the invention may be applied by any appropriate route, in particular oral, parenteral or external topical, and their formulations are adapted by a person skilled in the art, in particular for cosmetic or pharmaceutical compositions.

Advantageously, the compositions according to the invention are intended for cutaneous topical administration, on at least some of the skin of the face or body. The cosmetic composition according to the invention may be used as a care product and/or as a skin makeup product. These compositions must therefore contain a physiologically acceptable medium according to the invention, i.e. a medium that is suitable for use in contact with human skin or skin appendages, without the risk of toxicity, incompatibility, or even allergic response.

Preferably, the composition according to the invention intended to be applied topically on at least some of the skin of the face or the body is in the form of an aqueous, hydro-alcoholic or oily solution, an oil-in-water or water-in-oil emulsion or a multiple emulsion, solution, suspension, microemulsion, aqueous or anhydrous gel, serum or a dispersion of droplets or a colloidal dispersion. These compositions may also be in the form of creams, suspensions or powders, suitable for application on the skin, the mucous membranes, the lips and/or the skin appendages. These compositions may be more or less fluid and be in the form of a cream, a lotion, a milk, a serum, a pomade, a cream, a paste, an ointment, or a foam. They may also be in solid form, such as a stick, a patch, or be applied on the skin in the form of an aerosol or a spray. They may be used as a skin care product and/or as a skin makeup product. These compositions may also be suitable for applications on the scalp and/or hair, and in particular shampoo, conditioner, styling lotion, treatment lotion, a cream or a styling gel, a lotion for hair, a mask, etc. The cosmetic composition according to the invention may be used in particular in treatments involving an application followed or not followed by rinsing, or in the form of a shampoo. It may also be in the form of a dye or a mascara to be applied with a brush or a comb, in particular on the eyelashes, eyebrows or hair.

These compositions also include any additive commonly used in the field of use envisaged, as well as adjuvants necessary for their formulation, such as co-solvents (ethanol, glycerol, benzyl alcohol, moistening agent . . . ), thickening agents, diluents, emulsifiers, antioxidants, coloring agents, sunscreens, pigments, fillers, preservatives, fragrances, odor absorbers, essential oils, trace elements, essential fatty acids, surfactants, film-forming polymers, chemical or mineral filters, hydrating agents or thermal waters, etc. It is possible, for example, to cite water-soluble polymers of the natural polymer type, such as polysaccharides, or polypeptides, cellulosic derivatives of the methylcellulose or hydroxypropylcellulose type, or synthetic polymers, polaxamers, carbomers, siloxanes, PVA or PVP, and in particular polymers sold by the Ashland company. In any case, a person skilled in the art will make sure that these adjuvants as well as the proportions thereof are chosen so as not to adversely affect the advantageous properties sought in the composition according to the invention. These adjuvants may, for example, correspond to 0.01 to 20% of the total weight of the composition. When the composition of the invention is an emulsion, the fatty phase may represent 5 to 80% by weight and preferably 5 to 30% by weight with respect to the total weight of the composition. The emulsifiers and co-emulsifiers used in the composition will be chosen from those conventionally used in the field considered. For example, they may be used in a proportion ranging from 0.3 to 10% by weight, with respect to the total weight of the composition.

It is understood that the active principle according to the invention may be used alone or in association with at least one other active principle, in a cosmetic composition.

Advantageously, the compositions capable of being used according to the invention may also include various active principles intended to promote the action of the active agent according to the invention, in particular for the prevention and/or treatment of disorders associated with the skin barrier function or for calming the skin.

It is possible to cite, in a non-limiting manner, the following classes of ingredients: other peptide active principles, plant extracts, healing, anti-aging, anti-wrinkle, calming, anti-free-radical, anti-UV agents, agents stimulating the synthesis of dermal macromolecules or energy metabolism, hydrating, antibacterial, antifungal, anti-inflammatory, anesthetic agents, differentiation modulating agents, cutaneous pigmentation or depigmentation, nail or hair growth stimulating agents, etc. Preferably, an agent having a calming activity or an agent stimulating the synthesis of dermal macromolecules, or an agent stimulating energy metabolism will be used. More specifically, the active principle is chosen from the bioactive peptide active principles, vitamins, phytosterols, flavonoids, DHEA and/or one of its precursors or one of its chemical or biological derivatives, a metalloproteinase inhibitor or a retinoid.

According to a third aspect, the invention also consists of a process for cosmetic treatment intended to protect the commensal microbial flora and/or limit the imbalance in the commensal microbial flora, characterized in that a composition containing a linseed extract is applied topically on the skin or skin appendages to be treated.

Specific embodiments of this cosmetic treatment process also result from the description above. Other advantages and features of the invention will become clearer in view of the examples provided for illustrative and non-limiting examples.

FIG. 1 shows, in the form of a histogram, the immunohistochemical detection of the expression level of antimicrobial proteins DEFB1 and LL-37 in the ex vivo skin treated or not treated with 1% linseed extract for 24 h.

EXAMPLE 1

Preparation of Active Principle from Linseed (*Linum usitatissimum* L.)

In a first step, 1 kg of linseed seeds (*Linum usitatissimum* L.) is ground in a grain grinder. The flour obtained (1 kg) is placed in the presence of 10 liters of hexane. The mixture is then stirred for 2 hours at room temperature in order to perform a delipidation of the raw material. After filtration and vacuum drying, the powder obtained is suspended in 800 ml of an alkaline aqueous solution (1/10 dilution) pH 10 containing 1% polyvinylpolypyrrolidone (Polyclar V ISP). This mixture is stirred for 2 hours at room temperature so as to enable the soluble fractions to be solubilized. After this extraction phase, the medium is clarified by centrifugation, then filtered on a plate. This filtrate, which contains the soluble fractions of the linseed, is then subjected to a protein precipitation by varying the ionic force in a neutral or acid medium, which makes it possible to remove the soluble carbohydrate components, the lipids and the nucleic acids. The medium is brought to pH 3.5. The supernatant is removed and the precipitate is then washed with ethanol, then the solvent is evaporated by vacuum drying.

At this stage, around 50 grams of light yellow powder of raw protein extract are obtained, containing:
Proteins: 78%
Carbohydrates: 20%
Lipids <2%

The protein-rich precipitate is placed in solution in 500 grams of water.

The raw protein extract is then subjected to a series of controlled and selective enzymatic hydrolyses in the presence of 0.5% PVPP (Polyclar V) and cysteine endopeptidases (2 g/l bromelaine and 2 g/l alcalase). After 2 hours of reaction at 50° C. then deactivation of the enzymatic cocktail for 2 hours at 80° C., the hydrolysate is filtered on plates of decreasing porosity, then on a sterilizing cartridge (0.2 μm).

A light-colored hydrolysate is then obtained, measured at 15 to 30 g/l of dry extract, which is then diluted so that the concentration of peptide compounds determined by the Lowry method is between 0.1 and 5 g/l and preferably between 1.5 and 3.5 g/l. The physicochemical analysis of the plant hydrolysate, which constitutes the active principle, shows that its pH is between 4 and 5, and preferably between 4 and 4.5. The linseed extract according to the invention has a dry extract content of between 1 and 8 g/l, and preferably between 0.1 and 5 g/l and includes between 0.1 and 5 g/l of peptide compounds by weight of dry extract and between 0.1 and 2 g/l of sugars by weight of dry extract, preferably the linseed extract according to the invention is diluted so as to contain between 1.5 and 3.5 g/l of peptide compounds by weight of dry extract and between 0.1 and 0.3 g/l of sugars by weight of dry extract.

EXAMPLE 2

Demonstration of the Activating Effect of the Linseed Extract According to Example 1 on the Expression Level of DEFB1 and LL37 Messenger RNA in Keratinocytes The objective of this study is to determine the influence of the linseed extract according to example 1 on DEFB1 transcript expression and on LL-37 transcript expression. To evaluate the expression level of DEFB1 messenger RNA and the expression level of LL-37 messenger RNA, real-time polymerase chain reaction (PCR) quantifications were performed.

Protocol

NHK cells (normal primary human keratinocytes) are treated with 1% linseed extract according to example 1, twice daily, for 48 hours or are not treated (control).

To evaluate the expression level of DEFB1 messenger RNA and the expression level of LL-37 messenger RNA, it is necessary to isolate the total RNA from the keratinocytes in culture, treated or not treated by the linseed extract according to example 1. The total RNA are then transformed into complementary DNA by the action of a reverse transcriptase enzyme. A quantification of the complementary DNA is then performed by real-time PCR by means of a STEPONEPLUS™ thermocycler (Applied Biosystems). This quantification makes it possible to determine the expression level of DEFB1 messenger RNA and the expression level of LL-37 messenger RNA.

Results

An increase by 31% of the expression level of DEFB1 messenger RNA and an increase by 23% of the expression level of LL-37 messenger RNA is observed in the cells after 48 hours of treatment with the linseed extract according to example 1, by comparison with the untreated cells.

Conclusion

The linseed extract according to example 1 increases the expression level of messenger RNA encoding DEFB1 and the expression level of messenger RNA encoding LL-37, in normal human keratinocytes.

EXAMPLE 3

Demonstration of the Activating Effect of the Linseed Extract According to Example 1 on the Expression of the Antimicrobial Protein DEFB1 and on the Expression of the Antimicrobial Protein LL-37 in Keratinocytes The objective of this study is to determine the influence of the linseed extract according to example 1 on the expression of the antimicrobial protein DEFB1 and the expression of the antimicrobial protein LL-37. For this, the expression level of the DEFB1 protein and the expression level of the LL-37 protein were evaluated by immunocytochemistry on keratinocytes treated for 24 hours with the 1% linseed extract according to example 1 or without treatment (control) and embedded in paraffin.

Protocol

NHK cells (normal primary human keratinocytes) cultivated. These cells are then fixed with 10% formol, then embedded in paraffin. The cell block is then cut into sections with a thickness of 4 μm with a microtome knife and are then transferred onto a slide.

The sections are removed from the paraffin with 100% xylene, then rehydrated in successive alcohol baths: 2 100% ethanol baths (EtOH) for 2 minutes, 1 95% EtOH bath for 2 minutes, 1 90% EtOH bath for 2 minutes and 1 $H_2O$ bath for 5 minutes. The slides are submerged in a citric acid buffer at 0.01 M pH 6 and heated to a light boil in order to facilitate access of the antibody to the protein of interest. The sections are incubated with 5% BSA for 30 minutes, then with the primary antibody: an anti-"DEFB1" polyclonal rabbit antibody ab14425 (Abcam, Cambridge, UK), diluted to 1/500 in PBS or an anti-"LL-37" monoclonal mouse antibody sc-166770 (Tebu Santa Cruz, Calif., USA) diluted to 1/75 in PBS, for 1½ hours while stirring and at room temperature.

After a plurality of washings with PBS, the sections are incubated with the secondary fluorescent antibody (anti-rabbit Antibody Alexa Fluor 488 A21206 (Invitrogen, Fisher)) diluted to 1/1000 in PBS for 1 hour at room temperature. The cell nuclei are marked with 0.3 µM 4'6'-diamidino-2-phenylindole (DAPI) (Molecular Probes). The sections are rinsed for 5 minutes in PBS. The expression of the antimicrobial protein DEFB1 and the antimicrobial protein LL-37 is detected by means of a fluorescence microscope (objective 40×).

Results

The results show that there is an increase by 118% of the expression of the antimicrobial protein DEFB1 and an increase by 136% of the expression of the antimicrobial protein LL-37 in keratinocytes treated with the 1% linseed extract according to example 1 after 24 hours, by comparison with untreated keratinocytes.

Conclusion

The linseed extract according to example 1 stimulates the expression of the antimicrobial protein DEFB1 and the expression of the antimicrobial protein LL-37 in keratinocytes.

EXAMPLE 4

Demonstration of the Activating Effect of the Linseed Extract According to Example 1 on the Expression of the Antimicrobial Protein DEFB1 and on the Expression of the Antimicrobial Protein LL-37 in Ex Vivo Skin The objective of this study is to determine the influence of the linseed extract according to example 1 on the expression of DEFB1 and on the expression of LL-37. To evaluate the expression level of DEFB1 and LL-37, an immunolabeling of DEFB1 and LL-37 on ex vivo skin sections was performed.

Protocol

Human skin biopsies are kept in culture ex vivo, then treated, twice daily for 24 hours, by topical application of 20 µl of a 1% solution of the linseed extract according to example 1 or not treated.

The skin biopsies are then fixed, then embedded in paraffin after passage through a Shandon Hypercenter XP automatic apparatus (Shandon, UK). The skin biopsies embedded in paraffin are then cut into sections having a thickness of 4 µm with a microtome knife, which are themselves transferred to a slide. The sections are removed from the paraffin with 100% xylene, then rehydrated in successive alcohol baths: 2 100% ethanol baths (EtOH) for 2 minutes, 1 95% EtOH bath for 2 minutes, 1 90% EtOH bath for 2 minutes and 1 $H_2O$ bath for 5 minutes. The slides are submerged in a citric acid buffer at 0.01 M pH 6 and heated to a light boil in order to facilitate access of the antibody to the protein of interest. The sections are incubated with 5% BSA for 30 minutes, then with the primary antibody: an anti-"DEFB1" polyclonal rabbit antibody ab14425 (Abcam, Cambridge, UK), diluted to 1/500 in PBS or an anti-"LL-37" monoclonal mouse antibody sc-166770 (Tebu Santa Cruz, Calif., USA) diluted to 1/100 in PBS, for 1½ hours while stirring and at room temperature. After a plurality of washings with PBS, the sections are incubated with the secondary fluorescent antibody (anti-rabbit Antibody Alexa Fluor 488 A21206 (Invitrogen, Fisher)) diluted to 1/1000 in PBS for 1 hour at room temperature. The cell nuclei are marked with 0.3 µM 4'6'-diamidino-2-phenylindole (DAPI) (Molecular Probes). The sections are rinsed for 5 minutes in PBS. The expression of the antimicrobial protein DEFB1 and the antimicrobial protein LL-37 is detected by means of a fluorescence microscope (objective 40×).

Results

The set of results is presented in FIG. 1.

The evaluation of the fluorescence obtained on the sections by immunohistochemistry shows that the skin biopsies treated with the linseed extract according to example 1 have a highly significantly significant (+240%) higher level of expression of DEFB1 and (+140%) of the expression of LL-37 by comparison with untreated skin biopsies.

Conclusion

A positive effect on the expression of the antimicrobial protein DEFB1 and on the expression of the antimicrobial protein LL-37 is obtained as a result of the treatment with the linseed extract according to example 1 on human skin biopsies.

EXAMPLE 5

Demonstration of the Effect of the Linseed Extract According to Example 1 on the Number and Secreting Activity of Lamellar Bodies in Ex Vivo Skin The objective of this study is to determine the influence of the linseed extract according to example 1 on the number of lamellar bodies, the antimicrobial protein storage site, present at the interface of the stratum *granulosum* and stratum corneum. To observe lamellar bodies, electron microscopy images obtained from an ex vivo skin section were produced.

Protocol

Human skin biopsies are kept in culture ex vivo, then treated, once daily for 24 hours, by topical application of 20 µl of a 1% solution of the linseed extract according to example 1 or not treated.

The skin biopsies are then fixed by means of a Karnovsky fixative buffer (Electron Microscopy Sciences, Hatfield, UK) for 1 hour at room temperature, then overnight at 4° C. After having been rinsed by a Sodium Cacodylate buffer at 0.1 M (Sigma, Steinheim, Germany), the biopsies are post-fixed in 1% Osmium tetroxide $OsO_4$ for 1 hour, then rinsed and dehydrated in successive alcohol baths. The samples are infiltrated and included in a low-viscosity Epon-Epoxy mixture.

The sections are produced by means of a microtome knife equipped with a diamond blade. The sections are then colored with uranyl acetate and lead citrate. The observation is performed with a transmission electron microscope at 60 keV.

Results

The observation of the electron microscopy images shows that the skin biopsies treated with the linseed extract according to example 1 have a larger number of lamellar bodies at the interface of the stratum *granulosum* and stratum corneum by comparison with untreated skin biopsies.

Conclusion

A positive effect on the number of lamellar bodies, the antimicrobial peptide storage site, is observed as a result of the treatment with the linseed extract according to example 1 on human skin biopsies.

EXAMPLE 6

Demonstration of the Antimicrobial Effect Produced by the Linseed Extract According to Example 1 in Keratinocytes on the Bacterial Growth of *Staphylococcus aureus*

The objective of this study is to determine the effect of increased synthesis of antimicrobial proteins produced by keratinocytes as a result of stimulation by the linseed extract according to example 1 on the bacterial growth of *Staphylococcus aureus*. For this, a radial diffusion test was performed.

Protocol

NHK cells (normal primary human keratinocytes) are treated with the linseed extract according to example 1, twice daily, for 24 hours, or are not treated (control). To produce a negative control, NHK culture medium not having had any contact with the cells is used. The supernatant of the cells is then recovered and 150 µl are used to soak a disk having a 6-mm diameter. The disks are then placed on a *S. aureus* culture seeded in the mass (4 disks for each condition and Petri dish). After 48 hours, a radial diffusion area is observed. Photographs of the inhibition areas are taken with the QImaging Micropublisher 3.3 RTV camera and their diameters are calculated by the Q-CAPTURE PRO7™ software program.

Results

The results show that there is a 19% increase in the diameter of the bacterial growth inhibition area after application of supernatant resulting from the culture of keratinocytes treated with the 1% linseed extract according to example 1 after 24 hours, by comparison with untreated keratinocytes.

Conclusion

The linseed extract according to example 1 enables inhibition of bacterial growth.

EXAMPLE 7

Demonstration of the Antimicrobial Effect Produced by the Linseed Extract According to Example 1 in Keratinocytes on the Bacterial Growth of *Staphylococcus aureus*

The objective of this study is to determine the effect of increased synthesis of antimicrobial proteins produced by keratinocytes as a result of stimulation by the linseed extract according to example 1 on the bacterial growth of *Staphylococcus aureus*. For this, a bacterial growth inhibition test was performed.

Protocol

NHK cells (normal primary human keratinocytes) are treated with the linseed extract according to example 1, twice daily, for 48 hours, or are not treated (control). To produce a negative control, NHK culture medium not having had any contact with the cells is used. The supernatant of the cells is then recovered and 200 µl are used and contaminated by a solution of *S. aureus*. This supernatant/*S. aureus* mixture is incubated for 3 hours at 37° C. then spread on TSA agar dishes. After 48 hours, *S. aureus* colonies have developed and are visible to the naked eye. Photographs of the dishes are taken with the QImaging Micropublisher 3.3 RTV.

Results

The results show that there is a 79% decrease in the number of *S. aureus* colonies developed under the condition in which the supernatant was obtained from a culture of keratinocytes treated with the 1% linseed extract according to example 1 after 24 hours, by comparison with untreated keratinocytes.

Conclusion

The linseed extract according to example 1 enables a reduction in the number of bacterial colonies.

EXAMPLES

Preparation of Compositions

Protective Calming Day Cream

| Brand names | INCI names | Weight % |
|---|---|---|
| Phase A | | |
| EMULIUM® Delta | Cetyl alcohol (and) Glyceryl Stearate (and) PEG-75 Stearate (and) Ceteth-20 (and) Steareth-20 | 4.00 |
| LANETTE® O | Cetearyl Alcohol | 1.50 |
| D C 200 Fluid/100 cs | Dimethicone | 1.00 |
| DUB 810C | Coco Caprylate/Caprate | 1.00 |
| DPPG | Propylene Glycol Dipelargonate | 3.00 |
| DUB DPHCC | Dipentaerythrityl Hexacaprylate/Hexacaprate | 1.50 |
| CEGESOFT® PS6 | Vegetable Oil | 1.00 |
| Vitamin E | Tocopherol | 0.30 |
| Phase B | | |
| Demineralized water | Aqua | qsf 100 |
| Glycerin | Glycerin | 2.00 |
| CARBOPOL® EDT 2020 | Acrylates/C10-30 Alkyl Acrylate Crosspolymer | 0.15 |
| KELTROL® BT | Xanthan Gum | 0.30 |
| Allantoin | Allantoin | 0.5 |
| Phase C | | |
| Sodium Hydroxide (10% sol.) | Sodium Hydroxide | 0.30 |
| Phase D | | |
| Demineralized water | Aqua | 5.00 |
| STAY-C® 50 | Sodium Ascorbyl Phosphate | 0.50 |
| Phase E | | |
| Butylene Glycol | Butylene Glycol | 2.00 |
| ROKONSOL MEP | Phenoxyethanol (and) Methylparaben (and) Ethylparaben (and) Propylparaben | 1 |
| Dekaben CP | Chlorphenesin | 0.20 |
| Phase F | | |
| GP4G | Water (and) Artemia Extract | 1.00 |
| Linseed extract according to example 1 | | 1.5 |

Prepare phase A and heat to 75° C. Prepare phase B by dispersing carbopol, then xanthan gum while stirring. Let rest until perfect homogeneity is obtained. Heat B to 75° C.

At 75° C., emulsify A in B under rotor-stator stirring. Neutralize with phase C under rapid stirring. After cooling at 40° C., add limpid phase D, then phase E (preheated to 40° C. and homogenized until perfect limpidity is obtained). The cooling is continued with light stirring until 25° C. and phase F is added.

2—Body Milk

| Brand names | INCI names | Weight % |
|---|---|---|
| PHASE A | | |
| MONTANOV ® L | C14-22 Alcohols (and) C12-20 Alkyl Glucoside | 3.00 |
| Waglinol 2559 | Cetearyl Isononanoate | 4.00 |
| TEGOSOFT ® TN | C12-15 Alkyl Benzoate | 3.00 |
| Apricot Seed Oil | *Prunus Armeniaca* (Apricot) Kernel Oil | 2.00 |
| Avocado Oil | *Persea Gratissima* (Avocado) Oil | 1.00 |
| ABIL ® 350 | Dimethicone | 1.00 |
| PHASE B | | |
| Demineralized water | Aqua (Water) | Qsf 100 |
| Allantoin | Allantoin | 0.5 |
| PHASE C | | |
| SIMULGEL ® EG | Sodium Acrylate/Acryloyldimethyl Taurate Copolymer (and) Isohexadecane (and) Polysorbate 80 Copolymer (and) Polysorbate 80 | 0.4 |
| PHASE D | | |
| ROKONSAL MEP | Phenoxyethanol (and) Methylparaben (and) Ethylparaben (and) Propylparaben | 1 |
| GERMALL ® 115 | Imidazolidinyl Urea | 0.20 |
| PHASE E | | |
| Linseed extract according to example 1 | | 1 |

The constituents of phase A and phase B are heated separately between 70° C. and 75° C. Phase A is emulsified in phase B while stirring. Phase C is added, at 45° C., with increased stirring. Phases D and E are then added when the temperature is below 40° C. The cooling is continued until 25° C. under a heavy stirring.

The invention claimed is:

1. A method for the treatment of irritations of the skin and skin appendages caused by microbial stresses by increasing an expression level of defensin and/or cathelicidin antimicrobial peptides without causing a toxic or allergic reaction of the skin, the method comprising:
   providing a composition comprising a linseed extract, obtained from hydrolysis of linseed proteins, and comprising at least 1.5 to 3.5 g/l of peptide compounds by weight of dry extract, 0.3 g/l or less of sugar by weight of dry extract and includes essentially peptide compounds having a molecular weight below 5 kDa, for pharmaceutical use, as an active antimicrobial agent in a physiologically acceptable medium; and
   topically applying an effective amount of the linseed extract onto irritated skin of a subject in need twice daily for 24 or 48 hours, thereby increasing the expression level of defensin and/or cathelicidin antimicrobial peptides, and resulting in the treatment of irritations of the skin and skin appendages caused by microbial stresses.

2. The method of claim 1, wherein the method maintains the equilibrium and favorable conditions of the ecosystem of the commensal microflora of the skin, and reinforces the chemical barrier function of sensitive skin and skin appendages, without causing a toxic or allergic reaction of the skin.

3. The method according to claim 1, comprising topically applying an effective amount of the composition to reduce the imbalance of the commensal microbial flora of the skin and skin appendages.

4. The method according to claim 1, wherein the composition includes the linseed extract at a concentration of between 0.05% and about 5%.

5. The method according to claim 1, wherein, after dilution in a physiologically acceptable solvent, the linseed extract contains between 1.5 to 3.5 g/l of peptide compounds by weight of dry extract and 0.3 g/l or less of sugar by weight of dry extract.

* * * * *